(12) United States Patent
Patel et al.

(10) Patent No.: US 11,207,222 B2
(45) Date of Patent: Dec. 28, 2021

(54) ABSORBENT ARTICLE INCLUDING REINFORCED BACKSHEET

(71) Applicant: KPR U.S., LLC, Mansfield, MA (US)

(72) Inventors: Harish Patel, Norfolk, MA (US); Vishal Narvekar, Mansfield, MA (US)

(73) Assignee: KPR U.S., LLC, Mansfield, MA (US)

( * ) Notice: Subject to any disclaimer, the term of this patent is extended or adjusted under 35 U.S.C. 154(b) by 728 days.

(21) Appl. No.: 15/492,197

(22) Filed: Apr. 20, 2017

(65) Prior Publication Data
US 2017/0304129 A1    Oct. 26, 2017

Related U.S. Application Data

(60) Provisional application No. 62/326,580, filed on Apr. 22, 2016.

(51) Int. Cl.
*A61F 13/514* (2006.01)
*A61F 13/15* (2006.01)

(52) U.S. Cl.
CPC .. *A61F 13/51478* (2013.01); *A61F 13/15203* (2013.01); *A61F 13/51484* (2013.01)

(58) Field of Classification Search
CPC ...... A61F 13/51484; A61F 2013/15154; A61F 5/485; A61F 5/40
See application file for complete search history.

(56) References Cited

U.S. PATENT DOCUMENTS

| | | | | |
|---|---|---|---|---|
| 4,499,131 A * | 2/1985 | Knox | ...... | A61F 5/485 428/68 |
| 4,847,134 A * | 7/1989 | Fahrenkrug | ...... | A61F 13/49 428/138 |
| 5,099,532 A * | 3/1992 | Thomas | ...... | A61F 5/485 5/484 |
| 5,227,218 A * | 7/1993 | Herum | ...... | A61F 5/48 150/158 |
| 5,249,320 A * | 10/1993 | Moretz | ...... | A61F 5/01 5/484 |
| 5,330,817 A * | 7/1994 | Arnott | ...... | A61F 5/485 428/85 |
| 6,069,097 A * | 5/2000 | Suzuki | ...... | A61F 13/49009 442/328 |
| 6,348,423 B1 * | 2/2002 | Griffiths | ...... | A61F 13/0206 442/123 |
| 6,374,435 B1 * | 4/2002 | Leininger | ...... | A61G 7/1026 5/81.1 C |
| 2008/0306462 A1 * | 12/2008 | Bruckner | ...... | A61F 13/45 604/365 |

FOREIGN PATENT DOCUMENTS

WO    WO-9425251 A1 * 11/1994    ....... A61F 13/51484

* cited by examiner

*Primary Examiner* — Catharine L Anderson
*Assistant Examiner* — Arjuna P Chatrathi
(74) *Attorney, Agent, or Firm* — Arent Fox LLP

(57) ABSTRACT

In some examples, an absorbent article includes a backsheet comprising one or more reinforced edges, which helps increase the tensile strength of the absorbent article.

13 Claims, 4 Drawing Sheets

ABSORBENT ARTICLE INCLUDING REINFORCED BACKSHEET

CROSS-REFERENCE TO RELATED APPLICATION

This application claims the benefit of priority to U.S. Patent Application No. 62/326,580, filed Apr. 22, 2016, titled Absorbent Article Including Reinforced Backsheet, which is incorporated herein by reference in its entirety for all purposes.

TECHNICAL FIELD

This disclosure relates to an absorbent article.

BACKGROUND

Absorbent articles may be configured to collect and/or absorb body fluid discharge, such as urine, aqueous body fluids, mucus, blood, menses, or cellular debris. Examples of absorbent articles include disposable diapers or diaper inserts, adult incontinent pads or briefs, feminine hygiene products, training pants, and other articles that may be disposed against a body surface, by infants or adults. Another example of an absorbent article is an underpad, which may be suitable for use with patient bedding to help protect a mattress from body fluid discharge. The underpad can be disposable in some instances.

SUMMARY

In one example, an absorbent article comprises a first layer that is fluid permeable; a second layer comprising an absorbent material; a third layer that is fluid impermeable, the second layer being positioned between the first and third layers; and a reinforcement layer configured to structurally reinforce the third layer, wherein the third layer has a greater surface area than the reinforcement layer. The third layer is positioned between the reinforcement layer and the second layer. The reinforcement layer comprises a plurality of portions. The reinforcement layer is configured to reinforce at least one edge of the third layer. In some cases, the reinforcement layer comprises a first portion adjacent to a first edge of the third layer and a second portion adjacent to a second edge of the third layer. The first and second edges are opposite edges of the third layer. The absorbent article can further comprise a third portion positioned between the first and second portions. The third portion is substantially centered between the first and second edges of the third layer. The absorbent article can further comprise a sheet of material, wherein opposite edges of the sheet of material are folded toward each other to define the third layer and the reinforcement layer. The sheet of material has a machine direction and a cross direction, wherein the sheet of material is folded along the machine direction to define the third layer and the reinforcement member. In some cases, the third layer has a machine direction and a cross direction, wherein the reinforcement layer has a longitudinal axis that extends in the machine direction. The reinforcement layer is adhered to the third layer. In some cases, the reinforcement layer is ultrasonically bonded to the third layer. The absorbent article has a greatest thickness in a region including the reinforcement layer. The absorbent article can further comprise a fourth layer that is moisture vapor permeable, the fourth layer being positioned between the second and third layers. In some cases, a first region of the absorbent article including the reinforcement layer has a greater tensile strength than a second region of the absorbent article that does not include the reinforcement layer.

In another example, an absorbent article comprises a top sheet that is fluid permeable; an absorbent core; a backsheet that is liquid impermeable and vapor permeable, the absorbent core being positioned between the top sheet and the backsheet, the backsheet comprising at least one reinforced edge. The absorbent article has a greatest thickness at a region including the at least one reinforced edge of the backsheet. The absorbent article can further comprise a reinforcement layer configured to reinforce the at least one edge of the backsheet. The reinforcement layer comprises a plurality of portions. The at least one reinforced edge of the backsheet comprises a first edge and a second edge, the reinforcement layer comprising a first portion adjacent to the first edge of the backsheet and a second portion adjacent to the second edge of the backsheet. The first and second edges are opposite edges of the backsheet. The reinforcement layer further comprises a third portion positioned between the first and second portions. The backsheet has a greater surface area than the reinforcement layer. The reinforcement layer is adhered to the backsheet. In some cases, the reinforcement layer is ultrasonically bonded to the backsheet. The absorbent article can further comprise a sheet of material, wherein opposite edges of the sheet of material are folded toward each other to define the backsheet comprising the at least one reinforced edge. The sheet of material has a machine direction and a cross direction, and wherein the sheet of material is folded along the machine direction to define the backsheet comprising the at least one reinforced edge. The backsheet has a machine direction and a cross direction, the at least one reinforced edge extending in the machine direction. The absorbent article further comprises a moisture vapor permeable layer positioned between the absorbent core and the backsheet. In some cases, a first region of the absorbent article including the at least one reinforced edge has a greater tensile strength than a second region of the absorbent article that does not include the at least one reinforced edge.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

An absorbent article described herein includes a plurality of layers. In examples described herein, one of the layers is a backsheet and another of the layers is configured to reinforce the backsheet. The reinforced backsheet may help strengthen the absorbent article, e.g., such that the absorbent article may have a strength (e.g., tensile strength) sufficient to lift a patient when the absorbent article is used to reposition the patient.

The absorbent articles described herein include a substrate upon and within which fluid discharge, e.g., liquid insult, may be applied and absorbed. For illustrative purposes, the absorbent article will be discussed in terms of patient care underpads; however, in other examples, the absorbent articles including a reinforced backsheet may be any absorbent product such as, for example, disposable diapers, training pants, feminine hygiene products (e.g., sanitary napkins, panty-liners, or both), adult incontinence products (e.g., adult briefs, pads, or both), protective underwear, pet training pads, and other products, disposable or otherwise, utilized to absorb fluids. Some absorbent articles including a reinforced backsheet described herein may be configured to be disposed against a body surface, by infants or adults, and may be worn in cooperation with garments or may be a product that can be used on its own.

Figure 1:
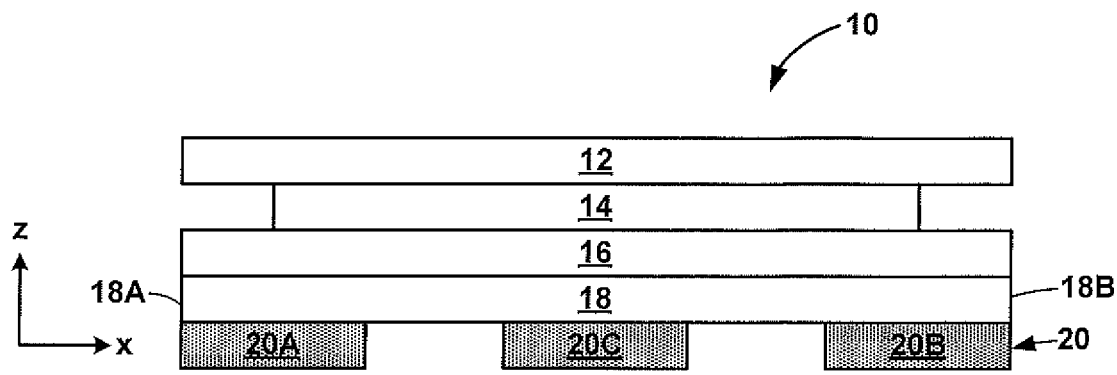
FIG. 1 is conceptual cross-sectional view of an example absorbent article that includes a reinforced backsheet.
Figure 2:
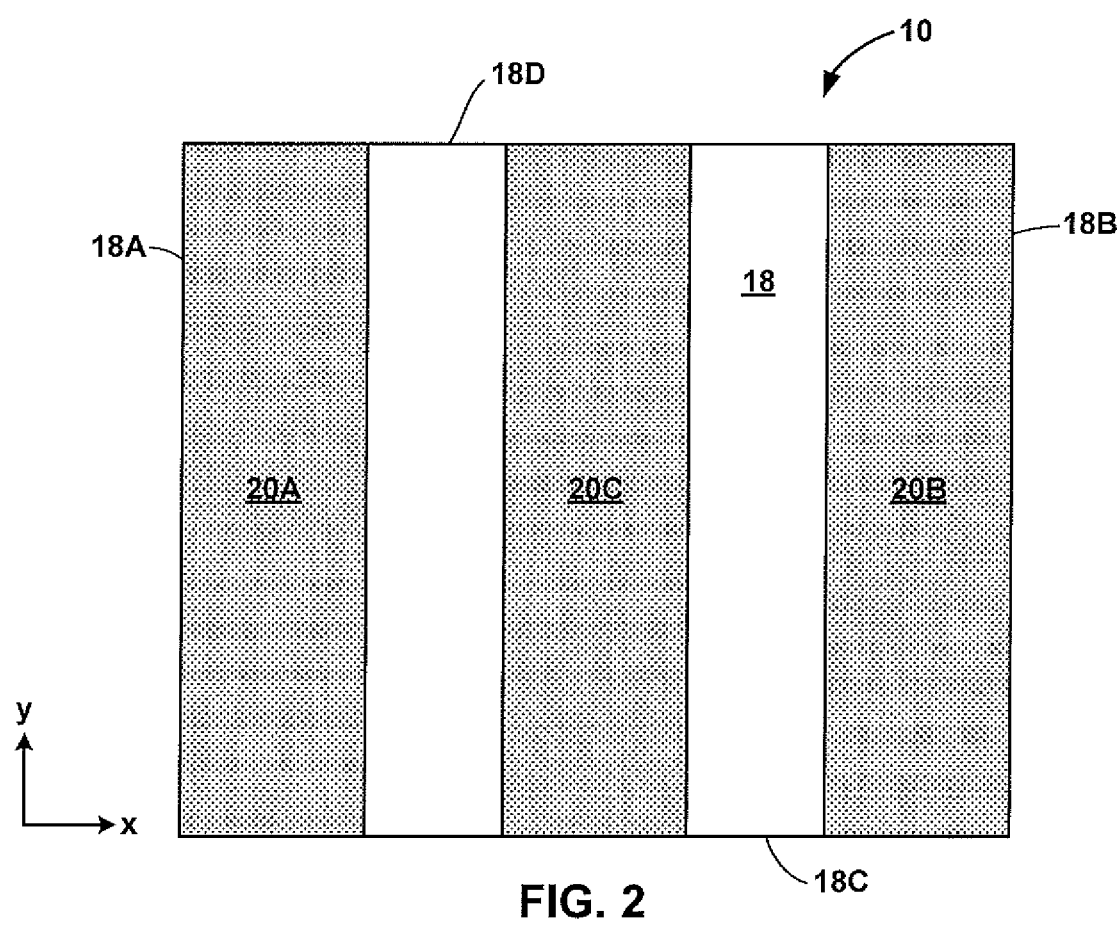
FIG. 2 is an elevation view of the absorbent article of FIG. 1.

FIG. 1 is a schematic cross-sectional view of an example multi-layer absorbent article 10, which includes top sheet 12, absorbent layer 14, moisture vapor permeable layer 16, backsheet 18, and reinforcement layer 20. FIG. 2 is an elevation view of absorbent article 10 and shows reinforcement layer 20 and backsheet 18. Although not illustrated to scale, absorbent article 10 may be, for example, a patient care underpad, which may have a sheet-like configuration (e.g., relatively thin compared to the width and length). The thickness is measured in the z-axis direction (orthogonal x-z axes are shown in FIG. 1 and orthogonal x-y are shown in FIG. 2 for ease of description only). When configured as an underpad, absorbent article 10 may be suitable for use with patient bedding to help protect a mattress from body fluid discharge, as well as to help improve patient comfort, such as by providing padding, by providing a relatively dry surface for the patient, even when absorbent layer 14 has absorbed fluids, or combinations thereof. In some examples, absorbent article 10 is used as a disposable product.

Top sheet 12 is fluid permeable, and is configured to allow a fluid to penetrate readily through its thickness. Top sheet 12 can be formed from any suitable material, such as a woven material, a nonwoven material, or a combination thereof. Suitable fibers that may be utilized to construct woven and non-woven materials for top sheet 12 include, for example, natural fibers, e.g., wood or cotton fibers; synthetic fibers, e.g., polymeric fibers such as polyester, polypropylene, or polyethylene fibers; and combinations of natural and synthetic fibers. The fibers may be fixedly secured to each other by adhesives, such as hot melt, or by other techniques, including, for example and without limitation, ultrasonic bonding, heat pressure sealing, and hot air knife bonding.

Example nonwoven materials include, but are not limited to, a non-woven web of fibers; polymeric materials such as thermoplastic films having apertures, plastic films having apertures, and hydro-formed thermoplastic films; porous foams; reticulated foams; reticulated thermoplastic films; and thermoplastic scrims. In examples in which top sheet 12 is a non-woven web, the web may be spun-bonded, carded, wet-laid, melt-blown, hydro-entangled, or formed using any method suitable for forming a non-woven web. In some examples, at least a portion of top sheet 12 can be formed of a nonwoven fibrous layer of polyolefinic fibers, which can be multicomponent fibers in some examples.

In some examples, top sheet 12 can include (e.g., be formed from or at least partially from) one or more bicomponent polymeric fibers. For example, top sheet 12 can be a fabric with first bicomponent fibers woven with second bicomponent fibers.

Top sheet 12, as well as article 10, may be compliant, such that it can relatively easily conform to a body of a patient when the patient is positioned on article 10. In the example shown in FIGS. 1 and 2, top sheet 12 defines a patient-interfacing surface of article 10. Thus, in some examples, top sheet 12 may be relatively soft in order to provide the patient or other user of article 10 with a comfortable interface and to minimize irritation to skin of the patient contacting top sheet 12. Although top sheet 12 is shown as the topmost surface of absorbent article 10 in FIG. 1, in other examples, absorbent article 10 can include one or more layers on top of the top sheet 12 (on the other side of the absorbent layer 14), or top sheet 12 can include more than one layer. For example, absorbent article 10 can include one or more additional fluid permeable and vapor permeable, or both fluid and vapor permeable layers on top of top sheet 12.

Absorbent layer 14 is positioned between top sheet 12 and backsheet 18, and is configured to absorb fluid that passes through top sheet 12. Absorbent article 10 can be placed against a patient (or other user) or against a patient's or user's clothing such that it is positioned to receive fluid discharge from the patient. When absorbent article 10 receives fluid discharge, such as an insult of fluid from the patient, a majority, or all, of the fluid may pass through top sheet 12 and be absorbed by absorbent layer 14. Absorbent article 10 can, but need not be, discarded after one insult of fluid.

Absorbent layer 14, which may also be referred to as an absorbent core in some examples, may comprise any one or more absorbent materials, such as, but not limited to, a foam, a nonwoven composite fabric, a hydrogel, a cellulosic fabric, a super absorbent polymer or other superabsorbent material, a woven fabric, paper, wood pulp, cotton linter and cotton wool of any suitable grade, rayon fibers, cotton staple, bleached or unbleached-creped tissue, and composites or other combinations thereof. Example foams include, but are not limited to, inherently hydrophilic foams, e.g., viscose rayon foam; natural or synthetic foamed polymeric materials, e.g., polyurethane, polyether, or styrene/butadiene rubber foams which have been rendered hydrophilic or readily wettable; or the like.

Example superabsorbent materials include, but are not limited to, starch type polymers, starch-graft polymers, cellulosic materials, and synthetic types, starch-acrylic acid (salt) graft copolymers, saponified starch-acrylonitrile copolymers, crosslinked sodium carboxymethyl cellulose, acrylic acid (salt) polymers, cross-linked polyacrylate polymers, polyacrylamides, polyethylene oxides, polyvinyl alcohols, polysuccinimides, hydrolyzed polyacrylonitriles, combinations thereof, and the like. In some examples, the superabsorbent material is a polymer selected from the group consistent of polyacrylamide, polyethylene oxide, polyvinyl alcohol, polysuccinimide, hydrolyzed polyacrylonitrile, and combinations thereof.

The super absorbent material can, for example, include super absorbent polymer particles. The particle diameter of super absorbent polymer particles can be from about 20 micrometers (μm) to about 850 μm, in some examples from about 110 μm to about 500 μm, in some examples from about 140 μm to about 350 μm. In some examples, the super absorbent polymer particles have an absorption speed of 45 seconds or less. When the absorption speed exceeds 45 seconds, so-called flow back may occur, where body fluids supplied to an absorber flow back outside the absorber.

In some examples, absorbent layer 14 is an embossed material that defines pockets (e.g., diamond-shaped or pockets of another shape) including an absorbent material, such as a mixture of fluff pulp material and superabsorbent polymer particles.

The material of absorbent layer 14 may be configured to define any suitable fluid distribution gradient in the z-axis direction, or the x- and y-axis directions, where the distribution gradient may affect how fluid flows through absorbent layer 14 (e.g., the speed of fluid flow, the direction of fluid flow, or both). For example, an absorbent or superabsorbent material having a faster absorption speed may be used in a central region of absorbent article 10 (e.g., central relative to the x- and y-axes), while an absorbent or superabsorbent material having a slower absorption speed may be used at the periphery. In other examples, absorbent layer 14 may be substantially uniform, such that the fluid distribution gradient is substantially the same throughout layer 14.

Moisture vapor permeable layer 16 is configured to allow at least some moisture vapor to escape or pass from absorbent layer 14 through moisture vapor permeable layer 16. The vapor permeability may help provide air circulation through absorbent article 10, which may minimize or even prevent vapor build-up. Moisture vapor permeable layer 16 may be formed from any suitable material, such as, but not limited to, a woven or nonwoven moisture vapor permeable material. In some examples, moisture vapor permeable layer 16 is also fluid impermeable, while in other examples, moisture vapor permeable layer 16 is at least partially fluid impermeable.

Backsheet 18 is substantially fluid impermeable (e.g., fluid impermeable or nearly fluid impermeable) and may help to prevent fluid leakages from absorbent article 10. Thus, backsheet 18 may help prevent liquid absorbed and contained in absorbent layer 14 from wetting an article that contacts backsheet 18 of absorbent article 10, such as, but not limited to, undergarments, pants, pajamas, or bed sheets. In addition, in some examples, backsheet 18 is air permeable (e.g., breathable) in order to allow at least some air to pass from absorbent layer 14, while substantially preventing fluid from passing through backsheet 18. The air permeability may help provide air circulation through absorbent article 10, which may minimize or even prevent vapor build-up. The air permeability may improve user comfort.

Backsheet 18 may be formed from any suitable material or combination of materials that alone or in combination provide a substantially liquid impermeable barrier for article 10. For example, backsheet 18 may include any one or more of: a woven material; a non-woven material; a liquid-impervious fabric; a cellulosic film; a polymeric film such as a thermoplastic film of polyethylene or polypropylene; an impregnated fluid repellent paper; a composite material, e.g., a polylaminate, such as a film-coated non-woven material; or combinations thereof. Although backsheet 18 is shown as one layer in FIG. 1, in other examples, backsheet 18 can include multiple layers. In some cases, backsheet 18 is comprised or consists of a polymeric film of, for example, polyethylene, and a nonwoven fabric of, for example, polypropylene. Further configurations involve backsheet 18 that is vapor permeable while being liquid impermeable. The basis weight of the backsheet 18 can be in a range of from about 10 grams per square meter (gsm) to about 40 gsm. In some examples, backsheet 18, or at least portions thereof, may be embossed or may be matte-finished to provide a cloth-like appearance, may be colored for ready identification, or both.

Absorbent article 10 includes reinforcement layer 20, which is configured to structurally reinforce backsheet 18 and increase the tensile strength of backsheet 18, as well as the tensile strength of absorbent article 10. For example, reinforcement layer 20 may help increase the amount of weight absorbent article 10 can support before tearing, rupturing, or otherwise failing, compared to examples in which an absorbent article only includes layers 12, 14, 16, and 18. Thus, when absorbent article 10 is used to lift a patient, e.g., to reposition a patient in bed or to move a patient from one bed to another, reinforcement layer 20 may help improve the performance of absorbent article 10, configure absorbent article 10 to be used to lift heavier patients compared to absorbent articles that do not include reinforcement layer 20, or improve the performance and configure absorbent article 10 to be used with heavier patients.

In some examples, the regions of absorbent layer including reinforcement layer 20 have a greater tensile strength than the regions of absorbent article 10 that do not include reinforcement layer 20. In some examples, reinforcement layer 20 has a greater tensile strength in at least one of the machine direction or the cross direction than one or more of top sheet 12, absorbent layer 14, moisture vapor permeable layer 16, and backsheet 18. In some cases, the reinforced portion or region of the absorbent layer has a tensile strength that is at least twice the tensile strength of the other, non-reinforced regions of the absorbent layer.

Reinforcement layer 20 is connected to backsheet 18 using any suitable technique. For example, reinforcement layer 20 may be adhered to backsheet 18 with an adhesive, reinforcement layer 20 and backsheet 18 may be ultrasonically welded together or melted together, or backsheet 18 and reinforcement layer 20 may be formed from a common sheet of material, as described with respect to FIG. 3.

As shown in FIG. 1, reinforcement layer 20 can be directly adjacent to backsheet 18 and may contact backsheet 18. In other examples, one or more additional layers may be positioned between backsheet 18 and reinforcement layer 20. In addition, as also shown in FIG. 1, backsheet 18 can be positioned between absorbent layer 14 and reinforcement layer 20. In other examples, however, reinforcement layer 20 can be positioned between absorbent layer 14 and backsheet 18, or absorbent article 10 can include another reinforcement layer between absorbent layer 14 and backsheet 18.

As shown in FIG. 1, absorbent article 10 has a greater thickness (as measured in the z-axis direction) at the regions including reinforcement layer 20 compared to regions that do not include reinforcement layer 20.

In the example shown in FIGS. 1 and 2, reinforcement layer 20 includes a plurality of portions 20A-20C. Portions 20A-20C can be, but need not be, substantially equal (e.g., equal or nearly equal) in size, as defined by the respective x-axis, y-axis, and/or z-axis dimensions. In FIGS. 1 and 2, portions 20A-20C are substantially equal in size and are substantially equally spaced (e.g., equally spaced or nearly equally spaced) from each other. For example, central portion 20C can be substantially centered (e.g., centered or nearly centered) between portions 20A, 20C. In other examples, portions 20A-20C may be unevenly distributed relative to backsheet 18, while still increasing the tensile strength of absorbent article 10.

Reinforcement layer 20 can, but need not, extend across either the entire span of backsheet 18 in at least one of the x-axis or y-axis directions in order to provide sufficient structural reinforcement to backsheet 18 to increase the tensile strength of backsheet 18, absorbent article 10, or both. Thus, in some examples, such as the example shown in FIGS. 1 and 2, a surface area of reinforcement layer 20, e.g., as provided by the surface area of each of the portions 20A-20C, is less than a surface area of backsheet 18. The surface area can be the surface area in the x-y plane. Configuring reinforcement layer 20 to have a smaller surface area than backsheet 18 may provide backsheet 18 with sufficient reinforcement, while reducing the weight reinforcement layer 20 adds to article 10, as well as reducing the cost of materials used to form article 10 compared to a reinforcement layer 20 that is the same surface area as backsheet 18.

In the example shown in FIGS. 1 and 2, portions 20A and 20B of reinforcement layer 20 structurally reinforce opposite edges 18A and 18B of backsheet 18, while portion 20C structurally reinforces a central portion of backsheet 18 between edges 18A, 18B. In addition, in the example shown in FIG. 2, because portions 20A-20C may each structurally reinforce opposite edges 18C, 18D of backsheet 18, reinforcement layer 20 may reinforce backsheet 18 in at least the y-axis direction, and, in some examples, both the x- and y-axes directions.

In some examples, backsheet 18 has a machine direction (e.g., the y-axis direction in the example shown in FIG. 2) and a cross direction (e.g., the x-axis direction in the example shown in FIG. 2), and a longitudinal axis of each portion 20A-20C may extend in the machine direction. For example, portions 20A-20C may each extend from edge 18C to edge 18D in the machine direction. A reinforcement layer 20 configured to reinforce backsheet 18 in the machine direction may help increase the tensile strength of absorbent article 10. In other examples, however, reinforcement layer 20 includes one or more portions that reinforce backsheet 18 in the cross-direction, or in both the machine- and cross-directions.

Although three portions 20A-20C are shown in FIG. 2, in other examples, reinforcement layer 20 can include any suitable number of portions, such as one, two, three, four or more portions. If reinforcement layer 20 includes one portion, the one portion can have a surface area less than backsheet 18 or multiple portions that together have a surface area less or equal to backsheet 18, while still providing sufficient structural reinforcement to backsheet 18 to improve the tensile strength of absorbent article 10.

While reinforcement layer 20 can have a surface area greater than backsheet 18 in some examples, such that reinforcement layer 20 extends past edges 18A-18D of backsheet, and, in some cases, extends past the edges of article 10, a reinforcement layer 20 having a smaller surface area than backsheet 18 may help prevent a user from grasping absorbent article 10 by only reinforcement layer 20 to lift a patient via article 10, and, therefore, may help prevent layer 20 from tearing, rupturing, or otherwise failing before the portion of article 10 including both backsheet 18 and reinforcement layer 20.

In some examples, portions 20A and 20B of reinforcement layer 20 extend to respective edges 18A, 18B of backsheet 18, such that reinforcement layer 20 includes portions aligned with opposite edges 18A, 18B of backsheet 18. In addition, portions 20A-20C extend from edge 18C to edge 18D of backsheet 18, such that reinforcement layer 20 includes portions aligned with the other edges 18C, 18D of backsheet 18. In other examples, however, one or more of portions 20A-20C can be inset relative to one or more of edges 18A-18D.

Figure 4:
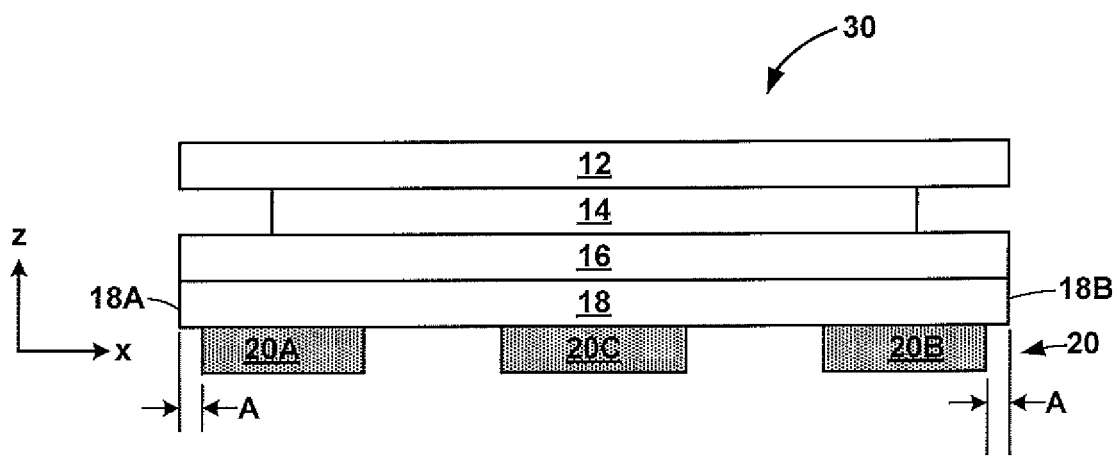
FIG. 4 is conceptual cross-sectional view of another example absorbent article that includes a reinforced backsheet.
Figure 5:
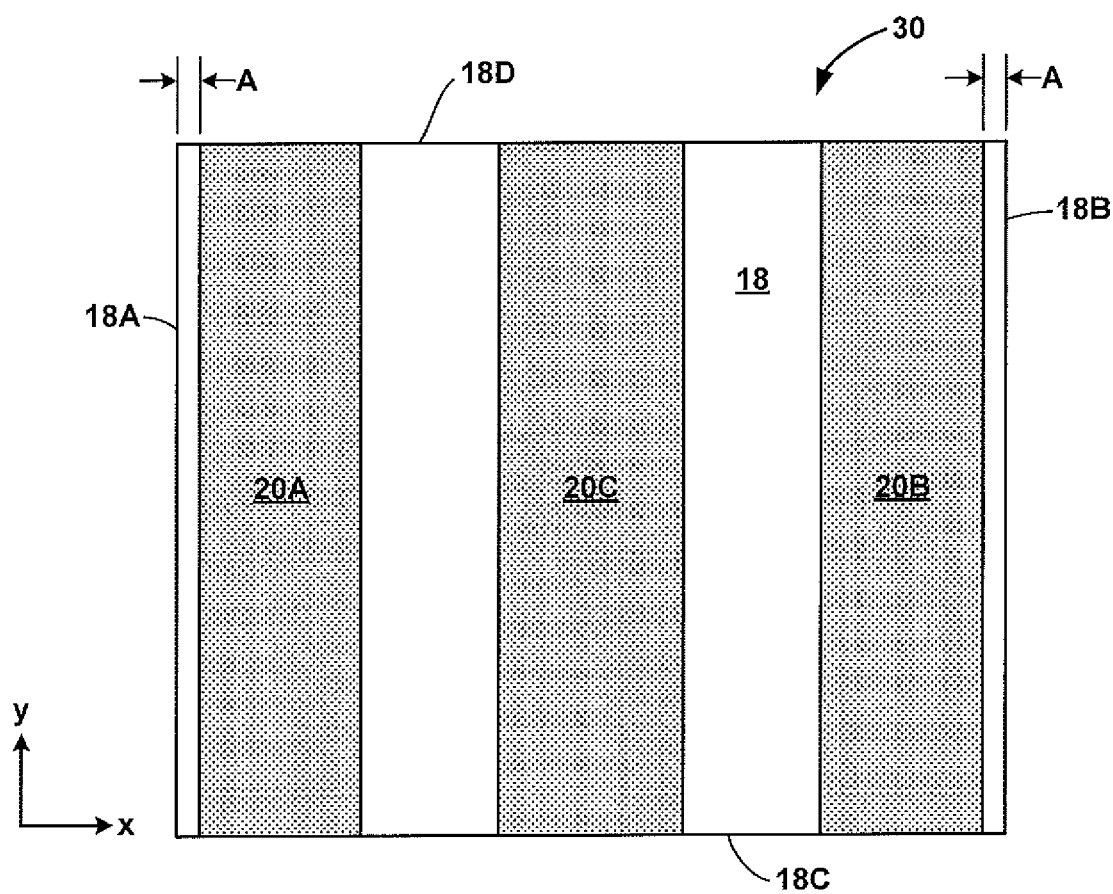
FIG. 5 is an elevation view of the absorbent article of FIG. 4.
Figure 6:
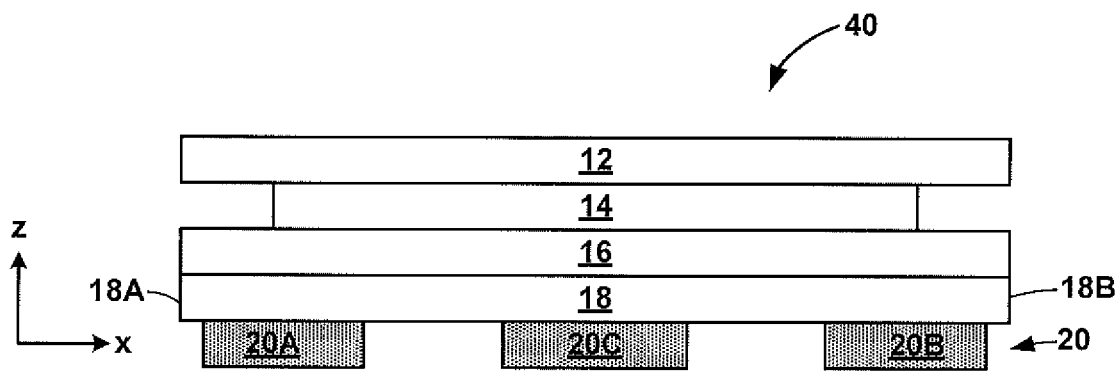
FIG. 6 is conceptual cross-sectional view of another example absorbent article that includes a reinforced backsheet.
Figure 7:
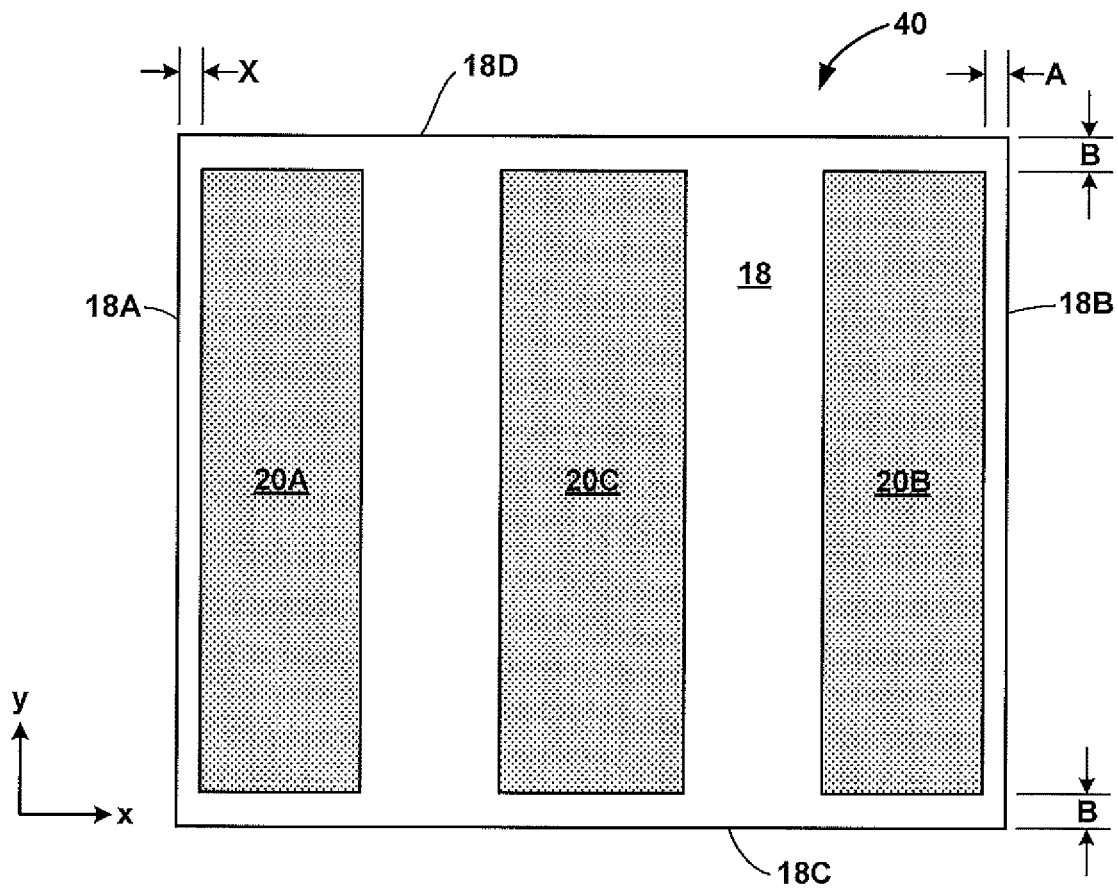
FIG. 7 is an elevation view of the absorbent article of FIG. 6.

FIGS. 4 and 5 illustrate an example absorbent article 30 in which portions 20A and 20B are inset relative to edges 18A, 18B. FIGS. 6 and 7 illustrate an example absorbent article 40 in which portions 20A and 20B are inset relative to all four edges 18A-18D, and portion 20C is inset relative to edges 18C, 18D. Of course, in other examples, absorbent articles can include a reinforcement layer 20 having other configurations, e.g., configurations in which one or more portions 20A-20C are inset relative to only one edge 18A-18D of backsheet 18, or two edges 18A-18D, which may or may not be opposite each other, or three edges 18A-18D.

The distance "A" by which one or more portions 20A, 20B are inset relative to an edge 18A or 18B and the distance "B" by which one or more portions 20A-20C are inset relative to an edge 18C or 18D may vary, but may be selected such that reinforcement layer 20 increases the tensile strength of the respective absorbent articles and helps prevent backsheet 18 or absorbent article 10 from tearing, rupturing, or otherwise failing when a user holds the absorbent article at or near its edges to lift a patient. Thus, distances "A" and "B" may be relatively small compared to the x-axis and y-axis dimensions of backsheet 18 such that portions 20A-20C substantially reinforce backsheet 18 from edge 18A to edge 18B and/or from edge 18C to edge 18D.

Figure 3:
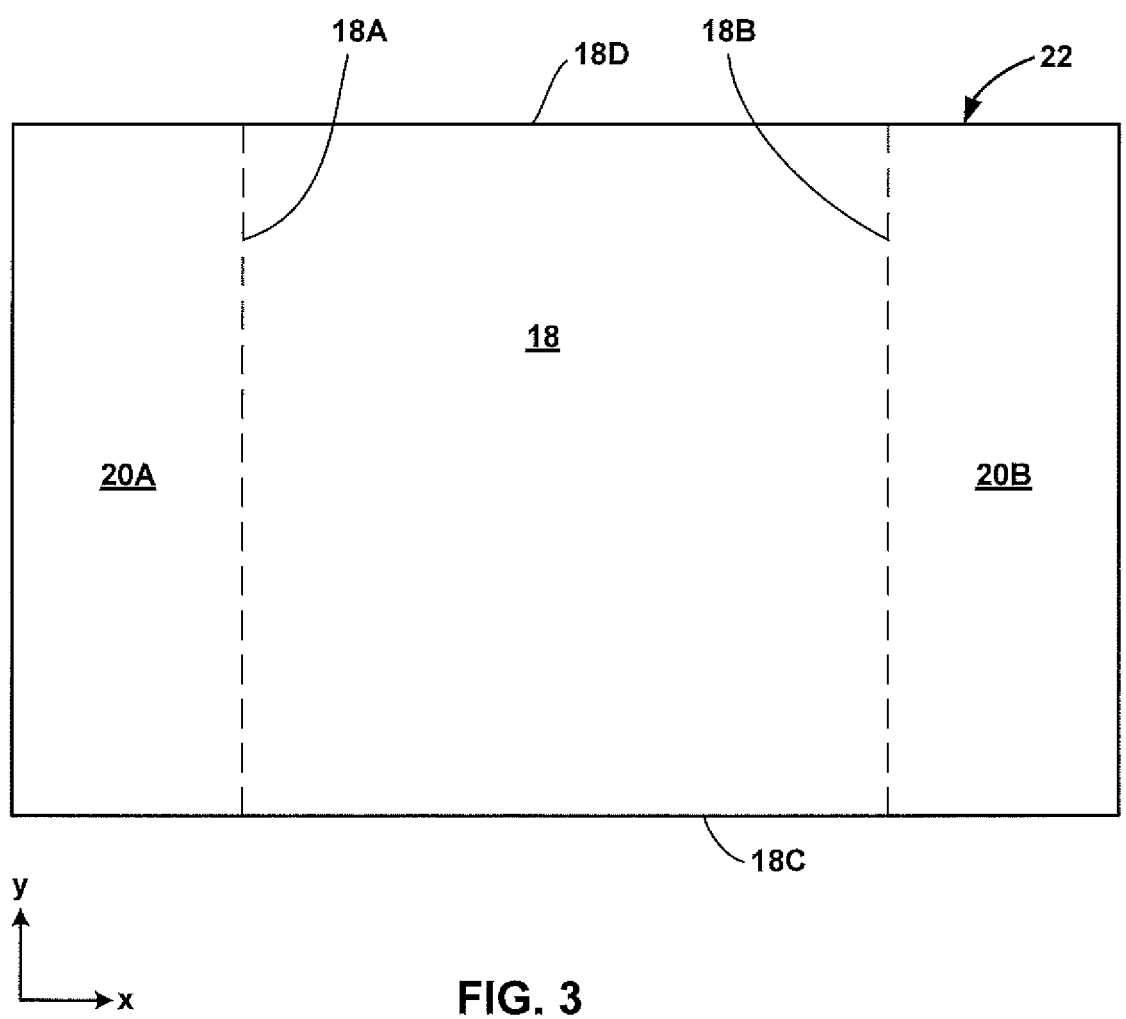
FIG. 3 is an elevation view of an example sheet of material that may be folded to define the backsheet and reinforcement layer of the absorbent article of FIG. 1.

Reinforcement layer 20 may be formed from any suitable material that, when connected to backsheet 18, increases the tensile strength of backsheet 18. In some examples, reinforcement layer 20 is formed from the same material as backsheet 18. For example, as shown in FIG. 3, at least a portion of reinforcement layer 20 can be formed by folding first and second edges of a sheet of material 22 defining backsheet 18 towards each other to define first and second opposite edges 18A, 18B of backsheet 18 and portions 20A, 20B of reinforcement layer 20. Sheet 22 can be folded in, for example, a machine direction, such that the material defining portions 20A, 20B of reinforcement layer 20 extend in a machine direction from one edge 18C of backsheet 18 to an opposite edge 18D. Sheet 22 can include one layer of material or can include multiple layers, which are folded together to define backsheet 18 and portions 20A, 20B of reinforcement layer 20. Once folded, portions 20A, 20B can be further connected to backsheet 18 using any suitable technique, such as by adhering the flaps that define portions 20A, 20B to backsheet 18, by ultrasonically welding the flaps to backsheet 18, by melting the flaps to backsheet 18, or any combination thereof.

In some examples, such as, but not limited to, examples in which sheet 22 is folded to define backsheet 18 and portions 20A, 20B of reinforcement layer 20, portions 20A, 20B are aligned with edges 18A, 18B of backsheet 18 and, in some instances, edges 18C, 18D. However, as discussed above, in other examples, one or more portions 20A-20C need not be aligned with edges 18A, 18B of backsheet 18, as shown in FIGS. 4 and 5 or with edges 18C, 18D of backsheet 18, as shown in FIGS. 6 and 7.

In other examples, rather than being formed from a unitary sheet 22 of material, reinforcement layer 20 can be formed separately from backsheet 18 and subsequently attached to backsheet 18, e.g. via an adhesive, ultrasonic welding, melting the materials together, or another suitable technique.

The absorbent articles described herein can be assembled using any suitable method. In one example, a method includes attaching absorbent layer 14 to a top sheet 12, and if being used, moisture vapor permeable layer 16, and attaching backsheet 18 to top sheet 12 and absorbent layer 14, and, if being used, moisture vapor permeable layer 16. In examples in which backsheet 18 and reinforcement layer 20 are formed from a common sheet 22 of material, backsheet 18 and reinforcement layer 20 are at least partially connected before backsheet is assembled to top sheet 12 and absorbent layer 14. In examples in which backsheet 18 and reinforcement layer 20 are formed separately and subsequently attached, however, the method can include attaching reinforcement layer 20 (e.g., the individual portions 20A-20C) to backsheet 18 prior to, after, or while attaching backsheet 18 to top sheet 12 and absorbent layer 14. The steps of the method described herein can be performed in any suitable order.

A method of using an absorbent article described herein can include, for example, positioning one or more absorbent articles 10, 30, 40 such that a patient is lying or otherwise on top of the absorbent article. For example, the absorbent article can be positioned between a patient and the patient's bedding. The method may further includes lifting the patient via the absorbent article by, for example, at least grasping near or at opposite edges of the absorbent article (e.g., edges corresponding to edges 18A, 18B and/or edges 18C, 18D of backsheet) and lifting the absorbent article on which the patient is positioned. Lifting the patient via the absorbent article can include, for example, repositioning the patient in a bed or transferring the patient from one bed to another bed.

Various examples have been described. These and other examples are within the scope of the following claims.

What is claimed is:

1. An absorbent article comprising:
a first layer that is fluid permeable;
a second layer comprising an absorbent material;
a third layer formed from a sheet of material having a first edge and a second edge,
wherein the first edge is folded over to provide a first portion of a reinforcement layer, the first portion consisting of a first folded-over portion of the third layer,
wherein the second edge is folded over to provide a second portion of the reinforcement layer, the second portion consisting of a second folded-over portion of the third layer,
wherein the third layer is fluid impermeable,
wherein the second layer is positioned between the first and third layers,
wherein the reinforcement layer consists of the first portion and the second portion,
wherein the reinforcement layer is configured to structurally reinforce the third layer, and
wherein the third layer has a greater surface area than the reinforcement layer.

2. The absorbent article of claim 1, wherein the third layer is positioned between the reinforcement layer and the second layer.

3. The absorbent article of claim 1, wherein the reinforcement layer is configured to reinforce at least one edge of the third layer.

4. The absorbent article of claim 1, wherein the first and second edges are opposite edges of the third layer.

5. The absorbent article of claim 1, wherein the sheet of material has a machine direction and a cross direction, and wherein the sheet of material is folded along the machine direction to define the third layer and the reinforcement layer.

6. The absorbent article of claim 1, wherein the third layer has a machine direction and a cross direction, and wherein the reinforcement layer has a longitudinal axis that extends in the machine direction.

7. The absorbent article of claim 1 wherein the reinforcement layer is adhered to the third layer.

8. The absorbent article of claim 1, wherein the reinforcement layer is ultrasonically bonded to the third layer.

9. The absorbent article of claim 1, wherein the absorbent article has a greatest thickness in a region including the reinforcement layer.

10. The absorbent article of claim 1, further comprising a fourth layer that is moisture vapor permeable, the fourth layer being positioned between the second and third layers.

11. The absorbent article of claim 1, wherein a first region of the absorbent article including the reinforcement layer has a greater tensile strength than a second region of the absorbent article that does not include the reinforcement layer.

12. An absorbent article comprising:
a top sheet that is fluid permeable;
an absorbent core;
a backsheet that is liquid impermeable and vapor permeable, the absorbent core being positioned between the top sheet and the backsheet,
wherein the backsheet comprises a first edge and a second edge,
wherein the first edge is folded over to provide a first portion of a reinforcement layer consisting of a first folded-over portion of the backsheet,
wherein the second edge is folded over to provide a second portion of the reinforcement layer consisting of a second folded-over portion of the backsheet, and
wherein the reinforcement layer consists of the first portion and the second portion.

13. The absorbent article of claim 12, wherein the absorbent article has a greatest thickness at a region including the reinforcement layer.

* * * * *